(12) United States Patent
Tuch et al.

(10) Patent No.: US 9,816,947 B2
(45) Date of Patent: Nov. 14, 2017

(54) SPECIMEN CHAMBER FOR OPTICAL IMAGING OF RADIOPHARMACEUTICALS

(71) Applicant: LIGHTPOINT MEDICAL LIMITED, Chesham (GB)

(72) Inventors: David Tuch, Hertfordshire (GB); Nicholas Collier, Cambridgeshire (GB); Kunal Vyas, Cambridgeshire (GB); Euan Morrison, Cambridgeshire (GB)

(73) Assignee: LIGHTPOINT MEDICAL LIMITED, Chesham (GB)

( * ) Notice: Subject to any disclaimer, the term of this patent is extended or adjusted under 35 U.S.C. 154(b) by 85 days.

(21) Appl. No.: 14/419,193

(22) PCT Filed: Aug. 5, 2013

(86) PCT No.: PCT/GB2013/052088
§ 371 (c)(1),
(2) Date: Feb. 2, 2015

(87) PCT Pub. No.: WO2014/020360
PCT Pub. Date: Feb. 6, 2014

(65) Prior Publication Data
US 2015/0241363 A1  Aug. 27, 2015

Related U.S. Application Data

(60) Provisional application No. 61/679,449, filed on Aug. 3, 2012, provisional application No. 61/763,884, filed on Feb. 12, 2013.

(30) Foreign Application Priority Data

Aug. 3, 2012  (GB) .................................. 1213827.7

(51) Int. Cl.
*G01N 21/00* (2006.01)
*A61B 5/00* (2006.01)
(Continued)

(52) U.S. Cl.
CPC ......... *G01N 23/043* (2013.01); *A61B 5/0077* (2013.01); *A61B 5/0084* (2013.01);
(Continued)

(58) Field of Classification Search
CPC ............... G01N 23/043; G01N 23/046; G01N 21/6428; A61B 5/0077; A61B 5/0084; G01T 1/22
See application file for complete search history.

(56) References Cited

U.S. PATENT DOCUMENTS 4,529,296 A * 7/1985 Taylor .................. G03B 27/326
                                                          206/316.1
5,728,041 A * 3/1998 Fowler, Jr. ........... A61G 13/108
                                                             600/21
(Continued)

FOREIGN PATENT DOCUMENTS

WO   2011/137247   11/2011
WO   2012/083503    6/2012

OTHER PUBLICATIONS

Zhong et al, International Journal of Biomedical Imaging, vol. 2011, Article ID 641618.*
(Continued)

*Primary Examiner* — Casey Bryant
(74) *Attorney, Agent, or Firm* — Foley & Lardner LLP; Mark J. Danielson

(57) ABSTRACT

Apparatus for optical imaging of Cerenkov luminescence from an object subsequent to the object receiving a dose of a radiopharmaceutical, the apparatus comprising: a light tight enclosure within which the object can be received at a sample location; an imaging means; a means to mitigate direct particle impingement between the sample location and the imaging means; and one or more optical elements for
(Continued)

transmitting Cerenkov photons from within the light tight enclosure to the imaging means.

39 Claims, 9 Drawing Sheets

(51) Int. Cl.
 *G01T 1/22* (2006.01)
 *G01N 23/04* (2006.01)
 *G01N 21/64* (2006.01)
(52) U.S. Cl.
 CPC ....... *G01N 21/6428* (2013.01); *G01N 23/046* (2013.01); *G01T 1/22* (2013.01); *G01N 2223/419* (2013.01)

(56) References Cited

U.S. PATENT DOCUMENTS

| 2001/0002141 | A1* | 5/2001 | Kobayashi | A61B 1/05 348/45 |
|---|---|---|---|---|
| 2006/0281992 | A1 | 12/2006 | Stothers | |
| 2011/0250128 | A1 | 10/2011 | Carpenter | |
| 2012/0220870 | A1 | 8/2012 | Gambhir et al. | |
| 2012/0276002 | A1* | 11/2012 | Yoo | A61K 49/0002 424/1.49 |
| 2013/0259339 | A1* | 10/2013 | Tian | G01T 1/22 382/131 |

OTHER PUBLICATIONS

Cheng, Z., Ph.D., "Biomedical Applications of Cerenkov Luminescence Imaging", MIPS Molecular Imaging Program, Stanford University, p. 33 of 45 (Hu, et al. 2010).
Search Report dated Dec. 3, 2012 in corresponding British Application No. 1213827.7.
Holland, et al., "Intraoperative Imaging of Positron Emission Tomographic Radiotracers using Cerenkov Luminescence Emissions", Mol. Imaging, Jun. 2011, 10(3), pp. 177-186.
Kothapalli, et al., "Endoscopic Imaging of Cerenkov Luminescence", Biomed. Optics Express, Jun. 1, 2012, 3(6), pp, 1215-1225.
Liu and Carpenter, et al., "Intraoperative Imaging of Tumors Using Cerenkov Luminescence Endoscopy", J. Nuclear Med., May 2012, pp. 1579-1584.
Robertson, et al., "Optical Imaging of Cerenkov Light Generation from Positron-Emitting Radiotracers", Phys. Med., Biol. , Aug. 2009, 54(16), pp. N355-N365.
Zhong et al., "Cerenkov Luminescence Tomography for In Vivo Radiopharmaceutical Imaging", Int'l. Journal of Biomed. Imaging, 2011, 6 pages.
International Search Report dated Nov. 6, 2013 in corresponding PCT/GB13/052088.
International Search Report dated Dec. 11, 2013 in corresponding PCT/GB13/052087.

* cited by examiner

S = Subject, LS = Blue-light source, BS = Beam splitter, BP = Band-pass filter, C1 = Camera1 (for illuminated image), C2 = Camera2 (for Cerenkov image), I1 = Image1, I2 = Image2, P = Image processing, RS = Radiation shielding, I = Final image S = Subject, LS = Blue-light source, BS = Beam splitter, DMD = Digital Micromirror Device BP = Band-pass filter, C1 = Camera1 (for illuminated image), C2 = Camera2 (for Cerenkov image), 1 = Image1, I2 = Image2, P = Image processing, RS = Radiation shielding, I = Final image, TR = Trigger, L1, L2, L3 = Lenses PD = Pulse duration, PI = Pulse interval, GO = Gating offset

SPECIMEN CHAMBER FOR OPTICAL IMAGING OF RADIOPHARMACEUTICALS

CROSS REFERENCE TO RELATED APPLICATIONS

This application is a U.S. National Phase patent application of PCT/GB2013/052088, filed Aug. 5, 2013, which claims priority to United Kingdom patent application Serial No. 1213827.7, filed Aug. 3, 2012, U.S. Provisional patent application Ser. No. 61/679,449, filed Aug. 3, 2012, and U.S. Provisional patent application Ser. No. 61/763,884, filed Feb. 12, 2013, all of which are hereby incorporated by reference in the present disclosure in their entirety.

FIELD OF INVENTION

This invention has to do with methods and apparatus for optical imaging of radiopharmaceuticals, in particular Cerenkov Luminescence imaging. In particular, the invention provides a sample imaging chamber that can be used, to image objects, for example biological specimens, using optical imaging of radiopharmaceuticals.

BACKGROUND

Robertson et al. (Phys Med Biol. 2009) observed that certain diagnostic radiopharmaceuticals used in nuclear medicine scans can also be imaged optically. Specifically, radiopharmaceuticals that emit charged particles (e.g., alpha and beta particles) generate detectable light due to the phenomenon of Cerenkov luminescence. Cerenkov photons are due to the deceleration of the charged particle in tissue. Optical imaging of charged particle-emitting radiopharmaceuticals is termed Cerenkov Luminescence Imaging (CLI).

CLI combines the advantages of optical imaging (including high spatiotemporal resolution and low cost and form factor) with the advantages of nuclear imaging (including molecular specificity and widespread commercial availability of radiopharmaceuticals). Optical imaging will be understood to include ultraviolet to infra-red wavelengths.

In would be desirable to use CLI in a surgical situation, for example to provide images to inform a surgeon during the course of a procedure. One technical challenge for performing CLI in this scenario is that the Cerenkov luminescence is in the visible spectrum between 400-800 nm. The background illumination in an operating theatre would interfere and dominate the Cerenkov spectrum. Also, the illumination would induce tissue auto-fluorescence in the visible spectrum which would overlap with the Cerenkov signal.

CLI methods and systems are described in: US 2011/0250128; Holland et al., Mol Imaging, 2011; Carpenter et al., J Nucl. Med, 2012; US2012/0220870; and Kothapalli et al., Biomedical Optics Express, Vol 3, No 6, 1 Jun. 2012.

It has also been proposed to use CLI to create 3D images by means of tomography, as described in WO 2012/083503 and in Zhong et al, International Journal of Biomedical Imaging, Vol 2011, Article ID 641618. WO 2011/137247 also describes a method of 3D imaging of Cerenkov luminescence, based on the intensity profile of the Cerenkov light.

SUMMARY OF INVENTION

The present invention is concerned with improved methods and apparatus for optical imaging of radiopharmaceuticals that are more practical for specimen imaging in clinical settings and/or provide images that are more useful for clinical analysis.

In particular, the present inventors have identified a need for rapid, good quality imaging of objects such as a tissue sample excised from a subject during an on-going surgical procedure. For example, during a procedure to remove abnormal (e.g. cancerous) tissue from a subject it would be very beneficial for a surgeon to be able to confirm prior to conclusion of the procedure that they have removed all of the abnormal tissue; a common problem in such procedures is that a marginal portion of the abnormal tissue is left behind, which must be removed in a further procedure once it is later detected. A proposal of the present invention is therefore to provide a sample inspection device and method that use Cerenkov luminescence imaging to inspect an excised sample to check that the margins of the sample are clear of abnormal tissue (e.g. cancerous cells). The aim is to provide a sample inspection device that can be made available in an operating theatre.

In a first aspect, the invention provides apparatus for optical imaging of Cerenkov luminescence from an object (e.g. a tissue sample) subsequent to the object receiving a dose of a radiopharmaceutical, the apparatus comprising:
  a light tight enclosure within which the object can be received at a sample location;
  an imaging means to view the inside of the enclosure; and
  one or more optical elements for transmitting Cerenkov photons from within the light tight enclosure to the imaging means;
  wherein the apparatus is configured to protect the imaging means from radiation impingement.

In order to protect the Cerenkov imaging means from radiation impingement, the apparatus may comprise a radiation shield disposed between the sample location in the enclosure and the imaging means. Alternatively or additionally, the imaging means may be positioned and/or oriented relative to the sample location to minimise radiation impingement on the imaging means.

The object to be imaged will typically be a biological object. Examples include biological specimens or samples such as tissue samples, other biological material specimens, plant materials, cells or animals such as rodents.

The light tight enclosure may take any of a number of suitable forms consistent with its role of at least substantially (and preferably completely) excluding ambient light from the inside of the enclosure where the object is received. It is preferred that the ambient light level received by the imaging means should result in a photon flux less than 10 times the photon flux from the radiopharmaceutical, otherwise it may be very difficult or impossible to see the Cerenkov image. More preferably the photon flux resulting from ambient light is no more than 10 times less than the radiopharmaceutical flux. The flux from the radiopharmaceutical (e.g. F18) will typically be between $10^3$ and $10^4$ photons/s/sr/cm$^2$.

The enclosure may, for example, be a light tight container such as a sample dish with a lid having opaque walls to exclude ambient light from the inside of the container. Conveniently, the container may be disposable. In this case, the optical elements may, for example, be a fibrescope with its distal end exposed to the interior of the container, for example through a sealed opening in a wall of the container or the container lid, and a proximal end connected to the imaging means outside the container.

More preferably, the enclosure is a light tight specimen imaging chamber that is intended to be reusable. The introduction to and removal of objects from the chamber may be facilitated by a door in a wall of the chamber that, when open, allows access to the inside of the chamber and when closed ensures a light tight seal with surrounding parts of the chamber to maintain the light tightness of the chamber interior for imaging the object. Conveniently, the chamber may be generally polyhedral in shape (for example cuboid) with one complete side wall (i.e. face) of the chamber opening to serve as the door.

To maintain the light tightness of the chamber there is preferably a seal around the entire perimeter of the door to provide the light tight seal between the door and surrounding parts of the chamber wall when the door is closed. The seal may be mounted on the door or on the surrounding walls of the chamber against which the door butts when closed. The seal may include components on the door and the surround that mate with one another when the door is closed. The seal is preferably a labyrinth seal.

In some embodiments there is a light sensor within the chamber that can be used to confirm whether or not the chamber is light tight once the door is closed. In other embodiments, images collected by the imaging means can be used for this confirmation (especially where the imaging means is configurable to collect illuminated images, as discussed below).

The enclosure and door should be constructed of completely opaque materials, for example, 2 mm thick steel sheeting. Additionally, the internal surfaces are preferably black with low reflectivity in order to absorb any stray light.

The sample location may simply be the floor of the chamber. Preferably, however, there is a sample platform mounted within the chamber on which the object can be placed. This approach can more surely locate the object in the correct position in the chamber relative to the optical element (e.g. lens) within the chamber that collects Cerenkov photons from the object for transmission to the imaging means.

In some embodiments, the position of the sample platform can be adjusted within the chamber relative to the optical element, for example to adjust the distance between the sample platform (and hence an object located on the platform) and the optical element. The closer the object is to the optical element (e.g. lens) during an imaging process the greater the spatial resolution of the resultant image but the smaller the field of view. For any given imaging process the sample platform position can be chosen based on the desired trade-off between special resolution and field of view. The spacing between the platform and the optical element may, for example, be adjustable between about 1 cm and 50 cm. The sample platform may be mounted on a motorised jack (e.g. a scissor jack) to provide this movement. In some embodiments the height of the jack can be adjusted using controls that are outside the chamber.

In some embodiments, the position of the sample platform may be adjustable in other dimensions to move the object laterally relative to the optical element whilst maintaining the same spacing between the optical element and the platform. This may be useful to bring different portions of an object into the field of view of the optical element.

In some embodiments the object may be placed in a frame in order to prevent the object from deforming and/or to spatially position and orient the object in a known way. The frame may consist of transparent solid plastic, transparent glass, and/or transparent plastic film. The frame may be shaped as cuboid in order to orient the object in orthogonal orientations.

The imaging means may be a charge-coupled device (CCD) camera. An electron-multiplying CCD (emCCD) camera is preferred to acquire the low light level CLI images. Possible alternative imaging means include intensified CCD, photon multiplier tube (PMT) array, or microchannel plates with electron collection by one or more electrodes.

When using an emCCD camera to image Cerenkov photons, the EM gain will typically be set to at least 100, preferably at least 200 and more preferably to about 300. Higher EM gains may be used. For example, for photon counting a gain of as much as 1000 might be used. When acquiring the Cerenkov images the emCCD camera will be cooled, typically to −80 to −100 degrees C.

Where the imaging means includes an image detector with a surface on which the Cerenkov photons impinge (e.g. the surface of a detector chip in a CCD camera), the imaging means is preferably positioned and/or oriented so that the image detector surface is offset from any radiation beam exiting the enclosure (e.g. offset from an aperture through which the optical elements transfer the Cerenkov photons to the imaging means). Additionally or alternatively the image detector surface may be oriented so that it is substantially parallel to the radiation beam exiting the enclosure (e.g. angled at less than 45 degrees to the beam and preferably between about 0 degrees and 20 degrees, more preferably between 0 degrees and 10 degrees of the beam direction). In some embodiments the image detector surface will be substantially normal to the wall of the chamber it is mounted adjacent to. This minimizes the cross-section of the detector surface that might be directly impinged by any stray radiation that escapes the chamber. The optical elements can be configured to collect Cerenkov photons from the chamber and turn them through an appropriate angle (e.g. 90 degrees) to impinge on the detector surface.

The imaging means (e.g. CCD camera) may be mounted on the chamber so that the chamber and camera, along with optical elements, can be provided as a single unit. This can also ensure a preferred orientation of the imaging means and its shielding relative to the chamber. The imaging means (and its shielding) may, for example, be mounted on the top of the chamber or on a side wall of the chamber.

The radiation shield, where used, helps to avoid interference from unwanted radiation, such as x-rays, or beta particles. Suitable forms of shielding include lead shielding and Boron-filled high density polyethylene for example. Other materials or composite structures that can block the unwanted radiation can also be used.

The radiation shield may be located in a single plane between the imaging means and the sample location. For example, the shield may be part of a wall of the light tight enclosure to the side of the enclosure where the imaging means is located. More preferably, the shield surrounds a majority of the sides of the imaging means. The shield may, for example, take the form of an enclosure within which the imaging means is housed, the optical elements transmitting Cerenkov photons from within the light tight enclosure to the imaging means within the shield enclosure.

The one or more optical elements for transmitting Cerenkov photons from within the light tight enclosure to the imaging means will typically include a lens within the chamber and a light tight optical conduit for transmitting Cerenkov photons (or other light) collected by the lens to the imaging means. In some embodiments, the lens may be outside the light tight enclosure, either directly in line with an aperture in the enclosure or offset from the aperture with a mirror adjacent to the aperture directing the light (e.g. Cerenkov photons) exiting the aperture onto the lens.

In some embodiments, the optical conduit may be a hollow conduit that is light tight with mirrors and/or lenses to guide the light. Internal surfaces could be painted black to minimise stray reflections. In some other embodiments the light conduit could be a coherent optical fibre bundle.

In some embodiments, the focus of the lens can be varied. Where the lens is inside the enclosure, manual focus controls may be provided outside the enclosure with a mechanical linkage to the lens within the enclosure. Preferably, however, the adjustment of the lens focus is motorised so that controls can be provided outside the enclosure to facilitate focusing the lens when the chamber is closed without the possibility of compromising the light-tightness of the enclosure with mechanical linkages between the controls and the lens.

In embodiments where the light (e.g. Cerenkov photons) from the chamber must be turned through an angle to impinge on the imaging means, the optical elements may include a mirror, prism or other such optical element within the light conduit to effect the change in angle Alternatively, the bending of the light path may be achieved by using a flexible coherent fibre bundle.

In many cases it will be useful for the operator of the apparatus to be able to view an illuminated image (e.g. an anatomical image such as a white light image) of the object (e.g. tissue sample) within the light tight enclosure before and/or during acquisition of Cerenkov images.

Prior to acquisition of the Cerenkov image this may be useful, for example, to ensure correct positioning of the object within the chamber and correct focus of the lens. During acquisition it may be useful in order to confirm that the object has not shifted and/or to provide sequences of illuminated and Cerenkov images that can be overlaid upon one another. This may be especially beneficial in cases where the object is to be manipulated during the imaging process (as discussed below) or where the object moves itself (e.g. if a live animal imaged), where the illuminated image can be used to register the Cerenkov images with one another (where the object has moved between one captured Cerenkov image and subsequent images). Particularly in the case of using an illuminated image pre-Cerenkov acquisition to ensure correct location of the object, the image may conveniently be a video image.

In order to obtain an illuminated image from within the closed chamber it is necessary to illuminate the interior of the chamber. Some embodiments of the invention therefore comprise one or more lights within the chamber, which may for example be LEDs. For a white light image, white lights (e.g. white LEDs) may be used. Alternatively, to achieve a near white image without the use of phosphors (which are preferably avoided due to afterglow), some embodiments use a combination of red, green and blue ('RGB') lights, which again may be LEDs. The light sources may themselves be within the chamber or light from external light sources may be transmitted to within the chamber, for example through optical fibres.

In embodiments where multiple illuminated and Cerenkov images are to be acquired alternately with one another (i.e. time multiplexed) it is necessary to "switch off" the white/RGB lights during periods of CLI acquisition. In preference to actually switching off the lights (e.g. LEDs), a mechanical shutter may be used to cover the light(s) during periods of CLI acquisition and to uncover the light(s) during periods of illuminated image acquisition. This approach has the advantage of near instantaneous "switching off" of the lights, avoiding problems that might otherwise result from the period of time it takes for a light to cease emitting once it is no longer powered.

The mechanical shutter will be synchronised to the image acquisition sequence. The shutter may, for example, be a rotating disc with regularly spaced cut outs round its circumference so that the disc can intermittently cover and uncover the light(s). The rotation of the disc can then be controlled to give the desired periods of light and dark within the chamber, with which the illuminated and Cerenkov image acquisitions can be synchronised. Where separate cameras are used for illuminated image acquisition and CLI respectively, a mechanical shutter may also be used for the CLI imaging means (to avoid damage to the imaging means during periods of illuminated image acquisition). The shutter for the CLI imaging means may also be a rotating disc. Conveniently, the CLI imaging means and the light source for illuminating the chamber can be arranged so that a single rotating disc can serve as a shutter for the imaging means and the light source.

During such time multiplexed illuminated image and CLI acquisition, typically the duration on CLI acquisition periods will be longer than illuminated image acquisition periods to allow time to capture an adequate Cerenkov image, given the much lower light intensity levels. The CLI acquisition period may many times as long as the illuminated periods, for instance about 3 to 20 times as long. For example, for a 10 Hz illuminated video rate, the illuminated period would take 17 ms, with 75 ms of CLI acquisition in-between frames. 8 ms are lost every cycle due to the shutter transition times. The CLI imaging is only enabled whilst the light shutter is firmly closed and not in transition.

In some embodiments the CLI acquisition does not commence immediately after the light is 'switched off' (e.g. covered by the shutter) to give time for any residual light in the chamber to disperse.

In some embodiments it may be desirable to employ two separate imaging means, one to capture the illuminated image and the other to capture the CLI image. In other embodiments, a single imaging means captures both images.

In the case where a single imaging means is used it will normally be desirable to switch the imaging means between an illuminated level image mode and a low light level image mode for capture of the illuminated and CLI images respectively. This is because the types of camera that are sensitive enough to detect Cerenkov photons are likely to be damaged if the same sensitivity settings are used for an illuminated image. Where a single camera is used, the level of light for the illuminated image is preferably low and may be achieved, for example, by using neutral density filters and pulse width modulation of LEDs.

For example, in the case of an emCCD camera, whilst it will be cooled significantly and the EM gain set to a relatively high level for CLI, the camera will typically be operated in a conventional CCD mode, with no EM gain, when capturing illuminated images. Furthermore, in order to avoid ghosting it would be necessary to raise the temperature of the sensor to ambient before cooling it down once more for the next CLI image.

In some embodiments of the invention, therefore, the imaging means is switched between operating modes (Cerenkov image capture and illuminated image capture modes) during operation, this switching being synchronised with the switching on and off (e.g. by the mechanical shutter) of the light(s) in the chamber as the apparatus switches back and forth between Cerenkov image capture and illuminated image capture.

In some use scenarios for the apparatus according to embodiments of the first aspect of the invention it may be desirable to manipulate an object within the closed chamber from outside the chamber, for example with one or more instruments or by hand. Accordingly, some embodiments of the invention comprise one or more ports in the chamber wall that allow access for a hand or instrument without damaging the integrity of the light tight chamber.

There may, for example, be conventional sealed glove ports in which a port has a glove attached to it, the glove extending into the chamber. A user can then insert a hand into the glove to access the object within the chamber. The glove is formed of an opaque material to avoid light leaking into the chamber through the glove.

Alternatively, gloveless ports (also called hand-assist devices), such as the GelPort™ (Applied Medical Co.), Endopath Dextrus (Ethicon Inc.), Lap Disc (Ethicon Inc.), or Omniport (Advanced Surgical Concepts Ltd) may be used. With this type of port a gloved hand or an instrument can be pushed through the port into the chamber, whilst the port retains a tight seal around the glove hand/wrist/arm or instrument.

Particularly where the apparatus is to be used during a procedure for removing abnormal tissue, examination of the margins, especially the surface of the open surgical site can be important (as noted above). The inventors have recognised that there the sensitivity is reduced by the charged particles at the surface that escape the tissue and therefore cease generating Cerenkov photons. The sensitivity of CLI can be increased by placing a Cerenkov radiator on the surface of the tissue so that the escaping charged particles generate Cerenkov light. The Cerenkov radiator should have high refractive index ($1.5<RI<2.4$), high transmission at short wavelengths ($<500$ nm), and sufficiently thin to minimize scattering of the charged particles.

In some embodiments, therefore, it is proposed to use a Cerenkov radiator consisting of a cover slip or mesh with the properties indicated above. The Cernekov radiator can be placed over the tissue surface at the region of interest. The interaction with the cover slip or mesh of charged particles from the tissue surface generates Cerenkov photons and/or scintillation photons that can then be imaged by the imaging means.

Suitable high refractive index materials for the cover slip or mesh include lead glass, zirconium glass, or tellurite glass. A mesh is advantageous because it can better conform to an irregular-shape tissue surface. The mesh may be formed, for example, using discrete sections of high refractive index material held together by a flexible mesh lattice, for example of polyurethane.

In a second aspect, the invention provides a method for optical imaging of Cerenkov luminescence from an object (e.g. a tissue sample) subsequent to the subject receiving a dose of a radiopharmaceutical, the method comprising:
  placing the object in a light tight enclosure;
  illuminating the interior of the enclosure with light and capturing an illuminated image of the object in the enclosure whilst the interior of the enclosure is illuminated; and
  capturing a Cerenkov luminescence image of the object in the enclosure when the interior of the enclosure is not illuminated.

In some embodiments, a plurality of alternating illuminated and Cerenkov images are captured. In such cases, where the images are time multiplexed, the interior of the enclosure is intermittently illuminated, the illumination of the interior of the enclosure coinciding with capture of the illuminated images.

The illuminated image(s) and Cerenkov image(s) may be overlaid so that artefacts identified by the Cerenkov image can easily be related to a physical location on the object.

In some embodiments, the illuminated and Cerenkov images are captured by a single camera. The camera may have two modes, one for capture of the illuminated image and one for capture of the Cerenkov image. Preferably the camera is automatically switched between the two modes in synchronisation with the illumination (or not) of the interior of the enclosure.

In some embodiments the depth of the Cerenkov source is estimated by acquiring the image with different wavelength. This is possible where the wavelength-dependent absorption of the object is known.

The method may employ the apparatus of the first aspect above, including any one or more of its preferred and optional features discussed above.

Where illuminated and CLI images are produced they are preferably superimposed to produce a single image for use e.g. by a surgeon performing surgery to remove cancerous tissue that has taken up the radiopharmaceutical.

Where two separate imaging means are used, one for illuminated images and one for Cerenkov images, preferably the light paths feeding the two imaging means pass through a beam-splitter, so that they both image the same region of the object (e.g. tissue sample) at the same time. The beam-splitter is preferably a dichroic prism.

In such a dual imaging means arrangement, the Cerenkov imaging means may have a band pass filter to block any residual light and to aid in selecting the discrete and distinct wavelengths of light to be imaged. The need for the band pass filter may depend on the performance of the beam-splitter. The light in the chamber may use a filter to further minimize spectral overlap.

It will be understood by the skilled person that where two imaging means are used they can be contained within the same apparatus. For example, the two imaging means may be two different CCDs contained within the same unit. Using two imaging means has the advantage that it allows for the spectral response and dynamic range to be selected separately for each image. In addition, strong illumination of a sensitive camera increases the dark noise for a period after illumination. The CCD for the Cerenkov camera could have high quantum efficiency in the near infra-red range. The chip could comprise, for example, an electron multiplying CCD, intensified CCD, photon multiplier tube (PMT) array, or micro-channel plates with electron collection by one or more electrodes.

Preferably image processing is applied to the two images obtained from the first and second imaging means to calibrate the intensity windowing and apply image registration if required. To further segment the image from the second imaging means (i.e. the Cerenkov imaging means), additional imaging processing may be performed on this image including both spectral and spatial information. For example, it can be specified that the image from the second imaging means only comes from a restricted field-of-view (e.g. the sample location) within the image. Another example is that the signal within a pixel should fit the expected spectrum emitted from the radiopharmaceutical (e.g. the Cerenkov spectrum).

A third, more general aspect of the invention provides a method for optical imaging of Cerenkov luminescence from an object (e.g. tissue sample) subsequent to the object receiving a dose of a radiopharmaceutical, the method comprising the steps of:

illuminating the object with light from a light source;

capturing a first image whilst the object is illuminated with light from the light source; and capturing a second image whilst the object is not illuminated with light from the light source.

The object (e.g. tissue sample) and the light source may be within a light tight enclosure.

A fourth, more general aspect of the invention provides an apparatus for optical imaging of Cerenkov luminescence from an object subsequent to the object receiving a dose of a radiopharmaceutical, the apparatus comprising a first imaging means for capturing a first image of the object, and a second imaging means for capturing a second image of the object and means for illuminating the object, wherein the capture of the first and second images is time multiplexed, and said second image is captured when the object is not illuminated.

The means for illuminating the object may be a stroboscopic illuminating apparatus.

In some embodiments, the first image is obtained with a first imaging means and the second image obtained with a second imaging means. However it will be understood that the first and second images may be obtained with the same imaging means. This is important as it may reduce costs, as imaging means suitable for these applications can be expensive.

Preferably the time offset or gating offset between the strobe pulse and the acquisition of the second image is sufficiently long to allow for the decay of any induced tissue autofluorescence, and also for any charge on the imaging means (e.g. CCD) to be cleared.

Preferably the acquisition of the second image is gated off of a signal from the illumination system. The gated acquisition can be performed using, for example, a digital micro-mirror apparatus (DMD), a liquid crystal shutter or a spatial light modulator.

Preferably the object is illuminated by an automatic stroboscopic illumination. More preferably, the automatic stroboscopic illumination is white-light illumination with a gated shutter, for example, using a Pockels cell or digital micro-mirror apparatus (DMD).

Preferably the first image is an illuminated structural (e.g. anatomical) image and the second image is a Cerenkov image. In cases where the structural and Cerenkov images are measured by the same imaging means, the gated acquisition can be performed by treating segments of the signal as the Cerenkov image.

Preferably the plane of the imaging means (e.g. CCD) may be placed parallel to the incoming light to minimize the cross-section exposed to other sources of radiation such as x-rays or beta-particles.

Preferably the first and second images are calibrated. Preferably image processing is applied to the first and second images to calibrate the intensity windowing and apply image registration, if required. To further segment the image, additional imaging processing may be performed on this image including both spectral and spatial information. For example, it can be specified that the signal within a pixel should fit the expected spectrum emitted from the radiopharmaceutical (e.g. the Cerenkov spectrum).

If two imaging means are used, preferably the second imaging means is ultra-sensitive and is optimised to perform CLI. For example, preferably the second imaging means is a cooled, electron-multiplying CCD camera.

Preferably the light paths feeding the two imaging means pass through a beam-splitter, so that they both image the same region of the object. The beam-splitter is preferably a dichroic prism.

Preferably the second imaging means has a band pass filter to block any residual light and to aid in selecting the discrete and distinct wavelengths of light to be imaged. The need for the band pass filter may depend on the performance of the beam-splitter.

It will be understood by the skilled person that the first and second imaging means can be contained within the same apparatus. Preferably the imaging means is a camera. It will be understood by the skilled person that the imaging means could be a charge-coupled apparatus (CCD) contained within a camera. The first imaging means and the second imaging means may be two different CCDs contained within the same unit. Using two imaging means is preferable because it allows for the spectral response and dynamic range to be selected separately for each image. The CCD for the Cerenkov camera could have high quantum efficiency in the near infra-red range. The chip could comprise, for example, an electron multiplying CCD, intensified CCD, PMT array, or micro-channel plates with electron collection by one or more electrodes.

Preferably the second imaging means is also enclosed within a radiation shield (e.g. lead shielding or Boron-filled high density polyethylene) to block any interference from x-rays, or beta-particles.

Preferably the above aspects are such that they could also be applied in other diagnostic imaging procedures such as endoscopy, capsule endoscopy, imaging for robotic surgery, whole-body imaging, and basic research.

A further aspect of the invention provides a phantom, or testing replica, for ultra-weak light. The phantom may use a light emitting diode (LED) with one or more, for example a stack or layers of, neutral density filters through which light from the LED is emitted. Alternatively or additionally, a wavelength selective attenuator may be used in the LED. Reduction of intensity may alternatively or additionally be achieved using pulse width modulation, which may be varied using electronics or software techniques. The phantom may be used to calibrate the light system, and may also or alternatively be useful for maintenance and/or quality control.

BRIEF DESCRIPTION OF FIGURES

Examples are now described with reference to the accompanying drawings, in which.

DETAILED DESCRIPTION

Figure 1:
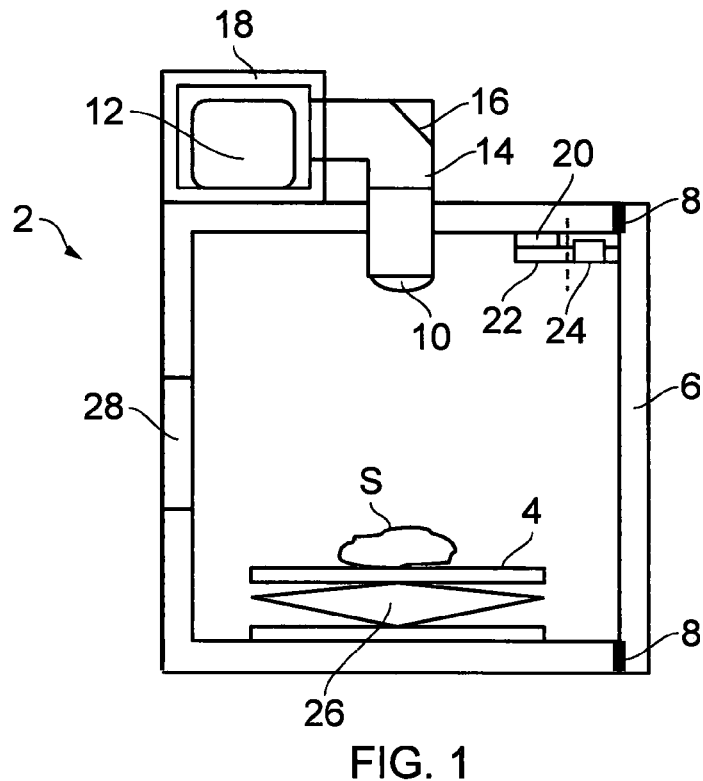
FIG. 1 shows schematically a specimen imaging chamber in accordance with an embodiment of the invention.

FIG. 1 shows a specimen imaging chamber apparatus in accordance with an embodiment of the invention that can be used to image an object, for example a tissue sample, using CLI. The invention will be exemplified with reference to imaging a tissue sample but the skilled person will understand that other objects may be imaged.

The apparatus includes a light tight chamber 2 in which a sample S can be supported on a sample platform 4. The chamber 2 has a door 6 that can be opened to give access to the interior of the chamber 2, for example for introduction of removal of a sample S. A seal 8, in this example a labyrinth seal, around the periphery of the door ensures the light tightness of the chamber when the door is closed.

An imaging system is mounted on the top of the chamber. This system includes a lens 10 that collects light from within the chamber (including light from the sample) and a camera 12. In this example, the camera is an emCCD camera. The lens preferably has a motor-driven focus, so that it can be focussed using a remote controller external to the chamber 2.

Light is transmitted from the lens 10 to the camera 12 through a light guide 14, which turns through a 90 degree angle. A mirror 16 in the light guide 14 deflects the light from the lens 10 to direct it onto an image detector (not shown) of the camera 12. With this arrangement, the surface of the image detector can be arrange to be normal to the top face of the chamber on which the camera is supported, so as to minimise the cross-section of the detector potentially exposed to x-rays or beta-particles escaping the chamber. To better protect the camera 12 from unwanted radiation, it is housed within a radiation shield 18.

The interior of the chamber 2 can be illuminated with illuminated (e.g. white light or RGB light) by one or more light sources 20 within the chamber. The light sources may be LEDs. With the chamber illuminated, the camera 12 can capture illuminated images (video or still) of the sample S in the chamber.

The illumination in the chamber 2 can be "switched off" by covering the light source(s) 20 with a mechanical shutter 22. In this example, the shutter is a rotatable disc that includes one or more openings 24. As the disc 22 is rotated is selectively uncovers and then covers the light source as the opening(s) 24 in the disc come into registration with the light source(s) 20. With the light source switched off, the imaging system can acquire low light level images such as Cerenkov images from a sample that has been dosed with a beta-emitting radiopharmaceutical.

Figure 5:
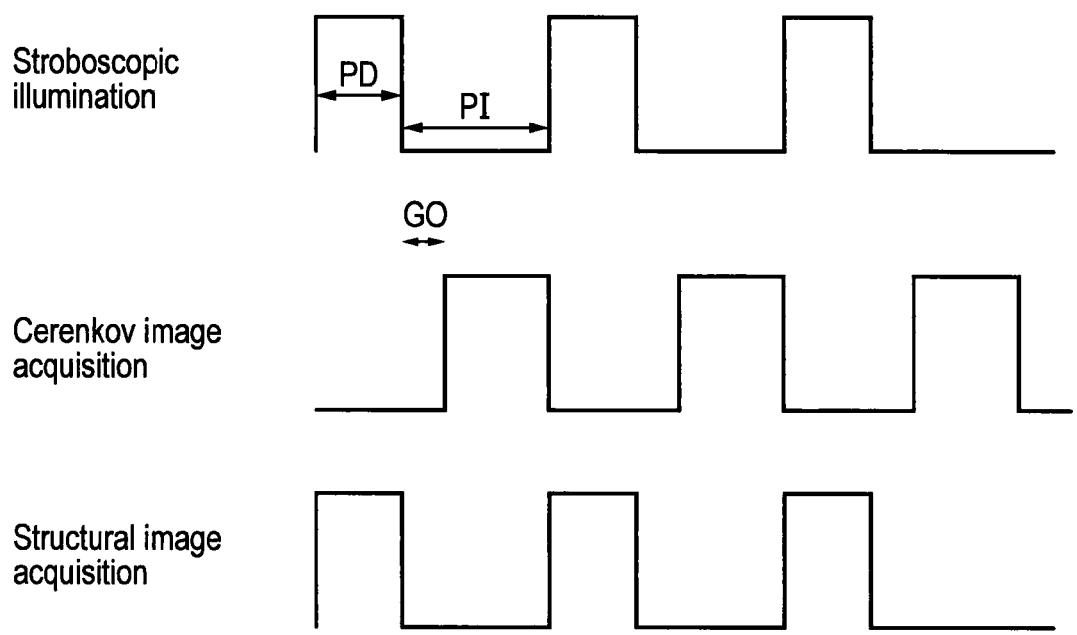
FIG. 5 shows an example sequence of stroboscopic illumination, Cerenkov image acquisition and structural image (e.g. illuminated) acquisition of an example embodiment of the invention.

FIG. 5 shows an example sequence of the stroboscopic pulses and intervals. In an example embodiment, strobe illumination may be >100 Hz and the pulse duration (PD) may be 10-1000 microseconds in an example embodiment. Structural image (i.e. illuminated image) acquisition is performed during the stroboscopic pulse duration. In this example embodiment the time or gating offset (GO) between the strobe pulse and the acquisition of the second image is sufficiently long to allow for the decay of any induced tissue autofluorescence, and also for any charge on the CCD of the camera to be cleared. In an example embodiment, if the pulse duration (PD) is 1000 microseconds, the pulse interval (PI) is 9000 microseconds, and so the gating offset (GO) may be 2000 microseconds and the second (Cerenkov) image acquisition time is 7000 microseconds. In another example embodiment, if the pulse duration (PD) is 10 microseconds, the pulse interval (PI) is 9990 microseconds and so the gating offset (GO) may be 1990 microseconds and the second (Cerenkov) image acquisition time is 8000 microseconds.

Figure 2:
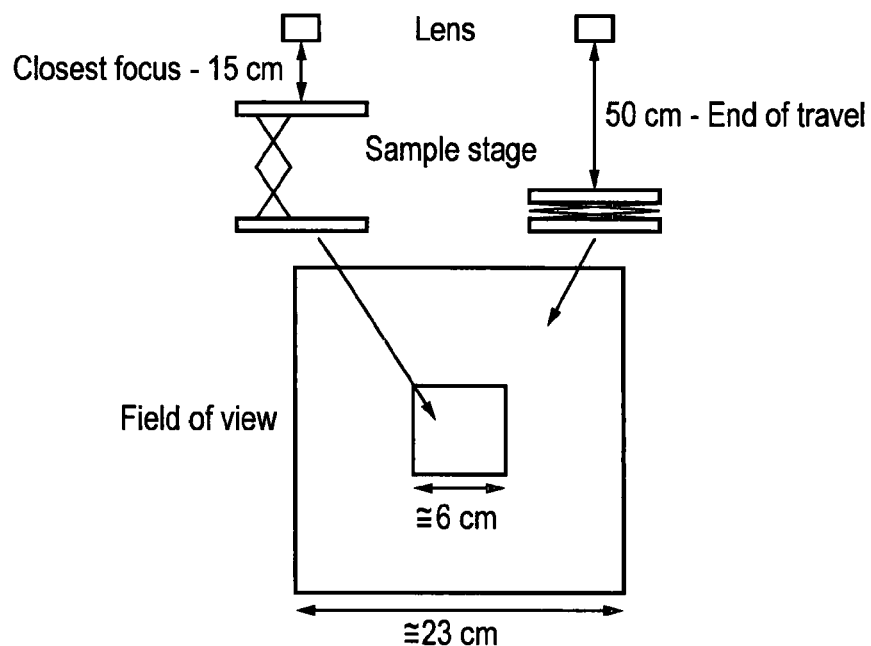
FIG. 2 schematically shows the effect of sample platform position on field of view for the specimen chamber of FIG. 1.

The sample platform 4 can be raised and lowered using a scissor jack 26 powered by an electric motor (not shown). The height of the platform can be adjusted to change the distance between the sample platform 4 (and hence the sample S on it) and the lens 10. As illustrated in FIG. 2, in this example this distance can be adjusted between 50 cm and 15 cm with a corresponding change in the field of view. As the field of view decreases, the physical resolution of the image increases.

The chamber also includes a light tight access port 28 through which the sample S can be accessed with an instrument of a gloved hand for example whilst maintaining the light tightness of the chamber 2. This access port may be a glove port for example.

As noted above, the specimen chamber apparatus uses an emCCD camera to acquire low light level images. Illuminated images are also captured with the same camera. To achieve this with the emCCD camera, one important aspect of the approach is to thermally cycle the camera when switching between low and high light levels. This is to ensure the camera does not experience high light levels when it is cooled in order to prevent ghost imaging. This is because the lifetime of photoelectrons is greatly enhanced at cold temperatures and the read out of stray photoelectrons from a bright image can be seen as noise in subsequent frames. This effect is long lasting and can adversely affect the signal to noise for many hours after exposure to illuminated.

The following is an exemplary procedure for acquiring images using the apparatus of FIG. 1.

1. Switch on camera and imaging software that drives it.
2. Open the door and adjust the sample stage to the desired height. This will depend on the desired field of view.
3. Load the sample
4. Ensure the door is properly closed to achieve a light tight enclosure.

Initially it may be useful to use a continuous (video) image from the camera in order to guide the choice of stage height used.

For Normal Illuminated Imaging:
5. Ensure the cooler for the camera is switched off.
6. Use camera settings suitable for normal light level imaging.

Typical Normal Illuminated Level Imaging Settings (Ambient Temperature)

| | |
|---|---|
| Readout rate | 3 MHz Conventional |
| Pre-Amplifier Gain | 3x |

-continued

| | |
|---|---|
| Vertical shift speed | 3.3 μs |
| Vertical clock voltage | Normal |
| EM gain | Disabled |
| Exposure time | 0.01 s |

7. Acquire a continuous live video image.
8. Switch on the internal lights—the light level is preferably adjustable so that it can be set such that the camera receives enough light without saturation.
9. Use the external focus controller to bring the target sample into sharp focus.
10. The image capture software may enable the image orientation to be changed if desired.
11. When happy, acquire a single still illuminated image.
12. Save the image.
   For Low Light Level Imaging:
13. Ensure the door is properly closed and ensure that the internal lights are switched off.
14. Switch on the camera cooler and set the temperature to −80° C.
15. Change the camera settings for low light level imaging.
   Typical Low Light Level Imaging Settings (−80° C.)

| | |
|---|---|
| Readout rate | 1 MHz Electron Multiplying |
| Pre-Amplifier Gain | 3x |
| Vertical shift speed | 0.5 μs |
| Vertical clock voltage | +1 |
| EM gain | $300_3$ |
| Exposure time | 5 s |

16. Before acquiring an image ensure the temperature has reached −80° C. and is stable.
17. Acquire an image.
18. The image quality can be enhanced by introducing on chip binning (e.g. 8×8 on chip binning for fast acquisition times). For higher resolution, the acquisition time can be increased.
19. For long integration times, when many photons per pixel can be collected, better results can often be obtained by using the conventional CCD mode:
   Typical Long Integration Time Settings (−80° C.)

| | |
|---|---|
| Readout rate | 80 kHz Conventional |
| Pre-Amplifier Gain | 3x |
| Vertical shift speed | 3.3 μs |
| Vertical clock voltage | Normal |
| EM gain | Disabled |
| Exposure time | >100 s |

20. Save the low light image.
21. Ensure EM gain is switched off before opening the door. The cooler should also be disabled to prevent ghosting during the next low light level acquisition.

Figure 10:
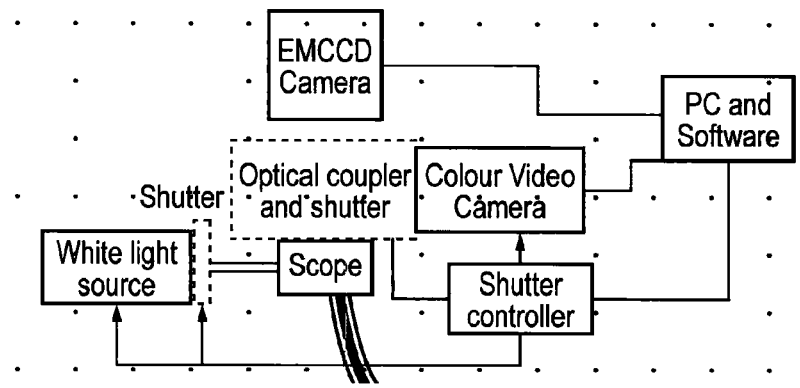
FIG. 10 schematically shows an arrangement that employs two cameras and an optical coupler and shutter to direct light to the two cameras.

FIG. 10 shows an alternative camera arrangement that could be used with the embodiment of FIG. 1, in which two cameras are used, an emCCD camera for CLI and a colour video camera for illuminated (e.g. anatomical) imaging. An optical coupler and shutter direct light to the two cameras and shutter is emCCD camera during periods when the interior of the chamber is illuminated. The shutter is controlled by a shutter controller to be synchronised with the illumination.

Figures 11A, 11B:
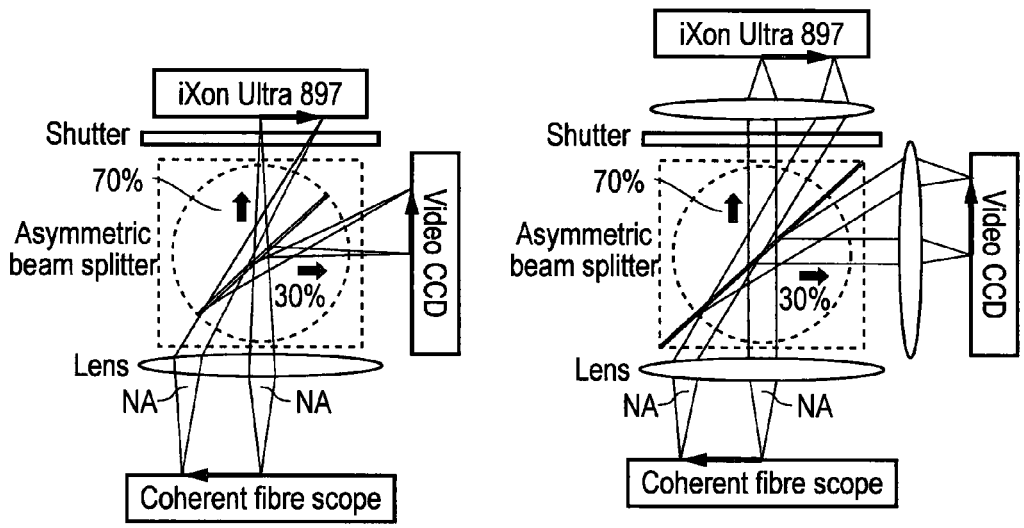
FIGS. 11a and 11b show two alternative arrangements for the optical coupler used in the arrangement of FIG. 10.

FIG. 11a shows one exemplary configuration for the optical coupler and shutter. In this example a single aspheric lens is used for coupling out of the fibre bundle and focussing on to both cameras. A high transmittance beam splitter option is shown.

FIG. 11b shows another option for the configuration of the optical coupler. In this example, a modular setup is used with a collimating lens coupling out of the fibre bundle and a focussing lens attached to each camera. The high transmittance beam splitter option is shown in this example too.

Figure 12A:
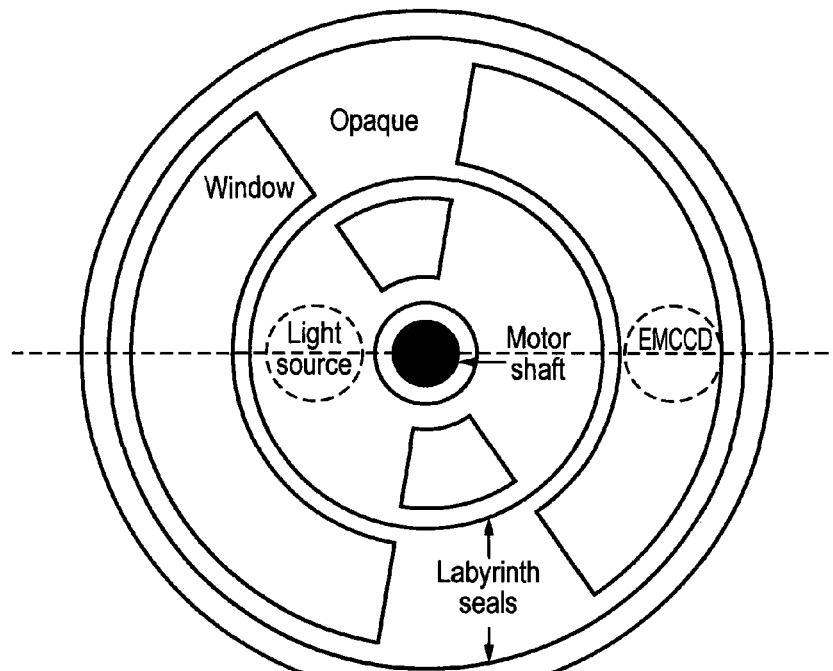
FIG. 12a shows a plan view and FIG. 12b a cross-section of a rotating disc shutter that can be used to shutter a light source and an emCCD camera.
Figure 12B:
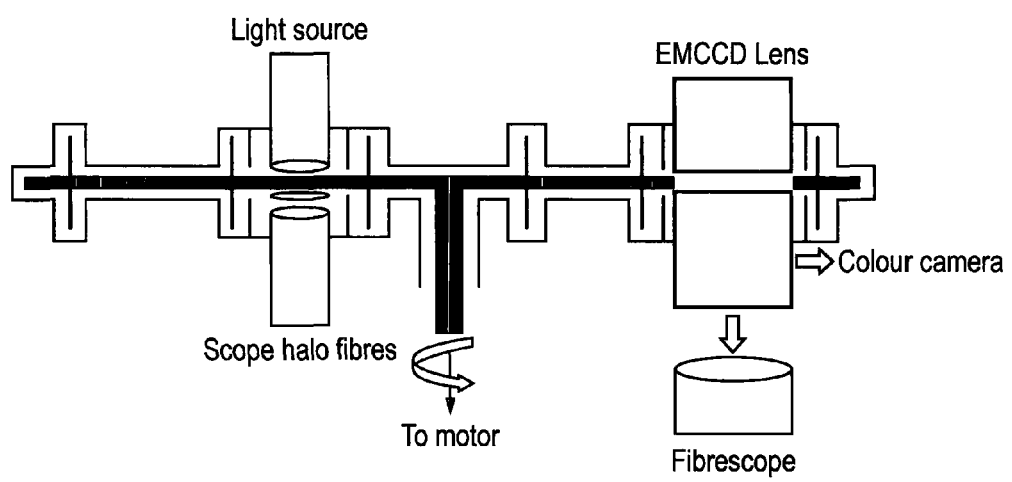

FIGS. 12a and 12b show an alternative shutter arrangement that can be used to shutter both the light source and the emCCD camera in embodiments where these two components are located adjacent to one another. The shutter is a rotating disc that is configured to cover both the light source and the emCCD lens. The disc is driven by a motor and as it rotates, windows in the disc, aligned respectively with the light source and the emCCD lens (which are at different radii) mean that the light source and the emCCD camera lens are selectively covered and uncovered. The relative positions of the windows ensure that the emCCD lens is covered when the light source is uncovered. As best seen in FIG. 12a, the emCCD windows are longer than the windows for the light source, to give a longer CLI acquisition period compared with the illuminated image acquisition period.

Figure 3:
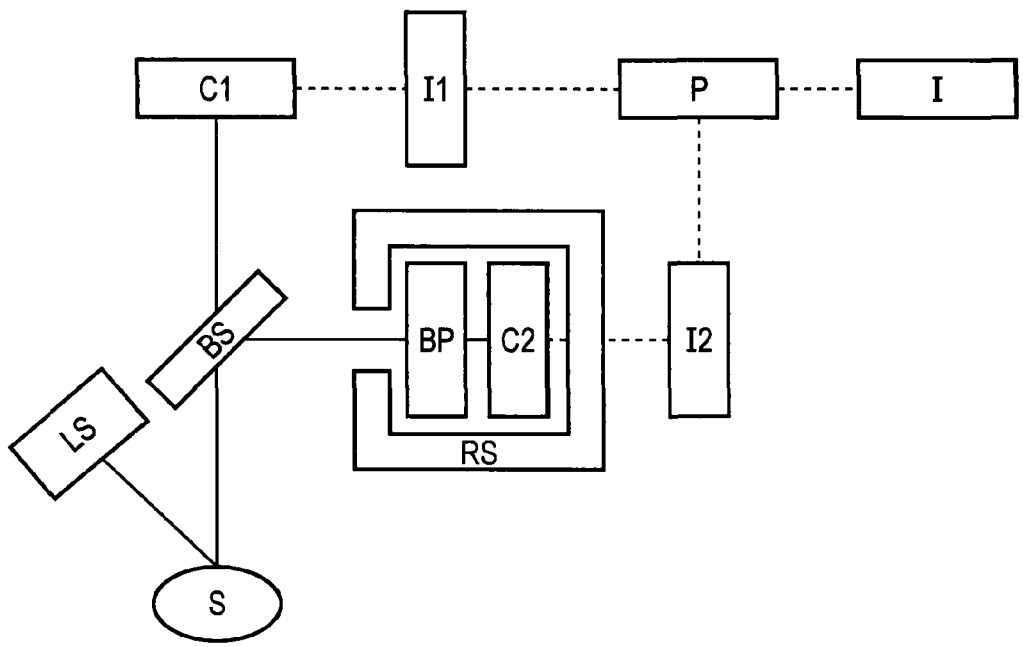
FIG. 3 schematically illustrates an embodiment in which two imaging means are used, which could be used in combination with a specimen chamber of the type shown in FIG. 1.

Turning to FIG. 3, we now discuss another embodiment of the invention. This example embodiment allows CLI to be performed under lit conditions. In this example embodiment, the background lighting is completely eliminated, and monochromatic red LED lighting is used to illuminate the object. However, the various features discussed, especially image acquisition using two cameras, could be used in embodiments of the invention using a specimen chamber as discussed above.

In this example embodiment, an object is injected with $^{18}$F-Fluorodeoxyglucose (FDG) (a common beta-emitting radiopharmaceutical). The radiopharmaceutical may be injected systemically, or locally. The injection may be intratumoral, peritumoral, or to the local arterial supply. Commonly, there is a narrow time window of around 60 to 90 minutes post-injection for a scan to be performed. This is a result of the use of radiopharmaceutical. Local injection directly has the advantage that it can lead to an earlier time window for performing CLI, and lower radiopharmaceutical dosage. A surgeon, for example, may choose to perform an image before carrying out a procedure, or perform a procedure then carry out imaging subsequently. The former may be useful, for example, for obtaining or confirming particulars, while the latter may be useful for checking the success of the procedure, for example.

Two separate cameras (C1 and C2) are used to image the illuminated image and the Cerenkov image respectively. Using two separate cameras allows for the spectral response and dynamic range to be selected separately for each image. The second camera (C2) is an ultra-sensitive camera such as a cooled CCD camera, which may be a cryogenically cooled CCD camera. For the first camera (C1), one or more monochromatic or colour cameras may be used. By rapidly applying (in any order) sequential red, green and blue illumination and then composing the image, full colour imaging can be provided. The speed at which the illumination is applied is determined by the desired frame rate of the video image.

In alternative embodiments, use of very low levels of illumination and a single camera may be used to take advantage of the sensitivity of the CLI camera. This illumination could be flashed red, green and blue if a colour image is required.

A CLI camera may have a light collector and/or lens to collect weak light. The light collector and/or lens may be built in to the camera. The lens may be a Fresnel lens. The light collector may be a shaped mirror. The mirror may be parabolic.

The light collector may be made of a material which has low scintillation for beta and gamma radiation. Scintillation is undesirable as it results in light being emitted that interferes with the signal.

A large aperture lens with low f number is preferred. This arrangement means that more light can be collected. Usually this is undesirable because it leads to distortions. However, it has surprisingly been found that the spatial resolution is sufficiently maintained for CLI, which generally has a comparatively poor spatial resolution, so that the improvement in light input outweighs the loss of spatial resolution.

The light reflected from the object is passed through a beam splitter (BS) such as a dichroic prism that directs the red light to the first camera and the non-red light to the second camera. The second camera is also equipped with a band-pass filter (BP) to block any residual red light. The need for the band-pass filter will depend on the performance of the beam-splitter. The role of red and blue may be reversed to allow, for example, a surgeon to see deeper into tissue.

C2 is also enclosed within a radiation shield (e.g., lead shielding) (RS) to block any interference from x-rays or beta-particles. The plane of the camera chip within C2 may also be placed parallel to the incoming light to minimize the cross-section exposed to x-rays or beta-particles.

Image processing (P) is applied to the two images (I1 and I2) to calibrate the intensity windowing and apply image registration, if required. To further segment the Cerenkov image, additional imaging processing can be performed on I2 including both spectral and spatial information. For example, it can be specified that the Cerenkov image only comes from a restricted field-of-view (such as the surgical site) within I2. Another example is that the signal within a pixel should fit the expected Cerenkov spectrum. The final image (I) is generated by superimposing the calibrated Cerenkov image (I2) on the illuminated image (I1).

In another embodiment of the invention, CLI can be performed in intervals between stroboscopic pulses of light. In this example embodiment, the object is illuminated by automatic stroboscopic illumination. In this embodiment the illumination is white-light illumination with a gated shutter using a digital micro-mirror apparatus (DMD). Other methods of shuttering are contemplated within the scope of the invention. In some embodiments, the strobed, or spectrally separated, lighting may be provided within an optical shroud. In some embodiments, the strobed, or spectrally separated, lighting may be provided in the room.

Figure 4:
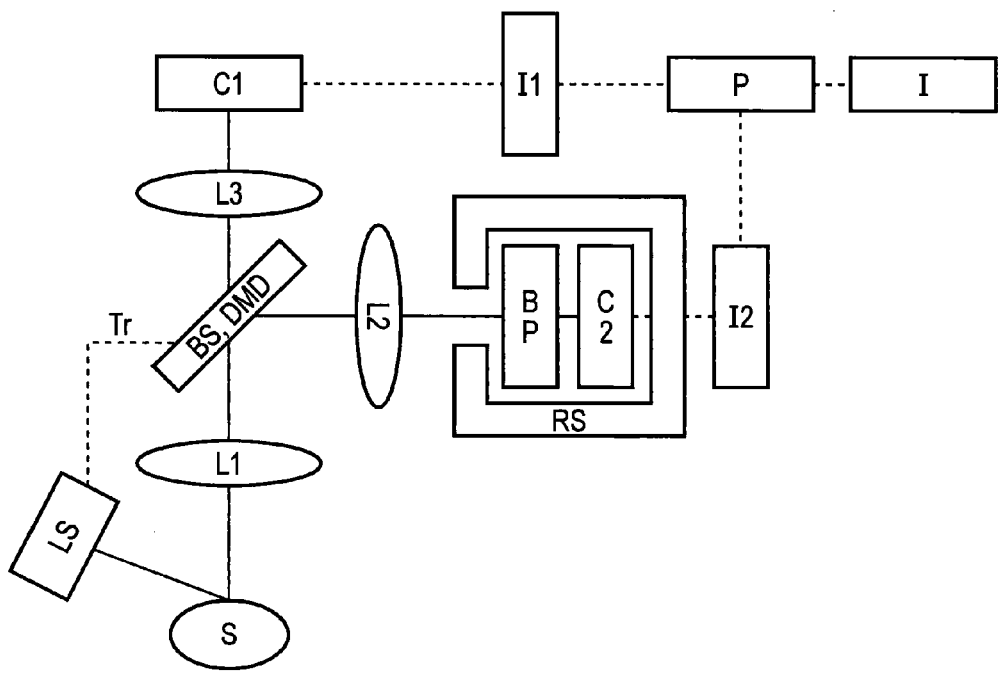
FIG. 4 shows an example embodiment of the invention that uses stroboscopic illumination.

This embodiment uses a similar apparatus setup to the embodiment described above. In this example embodiment the acquisition of the second image is gated off of a signal from the stroboscopic illumination system, as shown by FIG. 4. The gated acquisition is performed using a digital micro-mirror apparatus (DMD). In this example where stroboscopic illumination is used, a trigger (TR) connects the DMD to the light source. Connecting the light source and the DMD by the trigger allows light to be directed to one of two cameras for separate imaging of the Cerenkov or structural images.

FIG. 5 shows an example sequence of the stroboscopic pulses and intervals. In an example embodiment, strobe illumination may be >100 Hz and the pulse duration (PD) may be 10-1000 microseconds in an example embodiment.

Structural image (i.e. illuminated image) acquisition is performed during the stroboscopic pulse duration. In this example embodiment the time or gating offset (GO) between the strobe pulse and the acquisition of the second image is sufficiently long to allow for the decay of any induced tissue autofluorescence, and also for any charge on the CCD of the camera to be cleared. In an example embodiment, if the pulse duration (PD) is 1000 microseconds, the pulse interval (PI) is 9000 microseconds, and so the gating offset (GO) may be 2000 microseconds and the second (Cerenkov) image acquisition time is 7000 microseconds. In another example embodiment, if the pulse duration (PD) is 10 microseconds, the pulse interval (PI) is 9990 microseconds and so the gating offset (GO) may be 1990 microseconds and the second (Cerenkov) image acquisition time is 8000 microseconds.

In another embodiment of the invention, the camera system may also be implemented in an endoscope or "chip-in-tip" application, as shown in FIG. 4. In this embodiment, C1 is mounted within a fibre optic (FO). C1 is placed near the distal end of the endoscope, and light is transmitted to the proximal end to be read by C2. The beam-splitter may be placed on the distal end of the endoscope.

Figure 6:
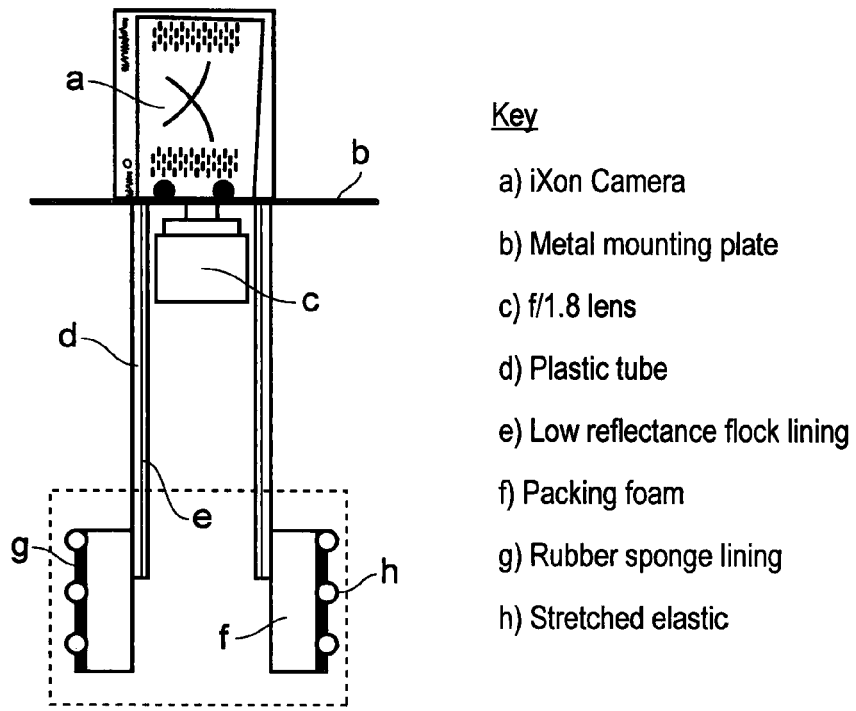
FIG. 6 is a schematic view of an optical light shield and camera setup used in experiments to illustrate the principles of embodiments of the invention.

FIG. 6 shows a schematic view of an exemplary optical light shield and camera setup in line with the present invention and used for the experiments discussed below. In this example, an iXon camera is positioned directly above a sample to be imaged (not shown) on a metal mounting plate b. An f/1.8 lens c is located beneath the camera and metal mounting plate b. A plastic (PVC) tube d extends between the metal mounting plate b and the sample to be imaged. The plastic tube d is lined with a low reflectance flock lining e. The sample is surrounded by packing foam g, which is covered with a neoprene rubber sponge lining g, in turn covered with stretched elastic h.

In some embodiments, a phantom, or testing replica, for ultra-weak light may be used to calibrate the light system. The phantom may use a light emitting diode (LED) with a stack or layers of neutral density filters. If necessary, the LED may be driven with a modulated waveform to further and controllably reduce the output of the LED. Such a phantom may also or alternatively be useful for maintenance and quality control of the light system.

The skilled person will appreciate that various modification to the specifically described embodiment are possible without departing from the invention. The following examples are used to support certain aspects of embodiments the invention.

Example

In vitro measurements of Cerenkov radiation emitted from F18 FDG were conducted using an iXon Ultra 897 emCCD camera.

Figure 7:
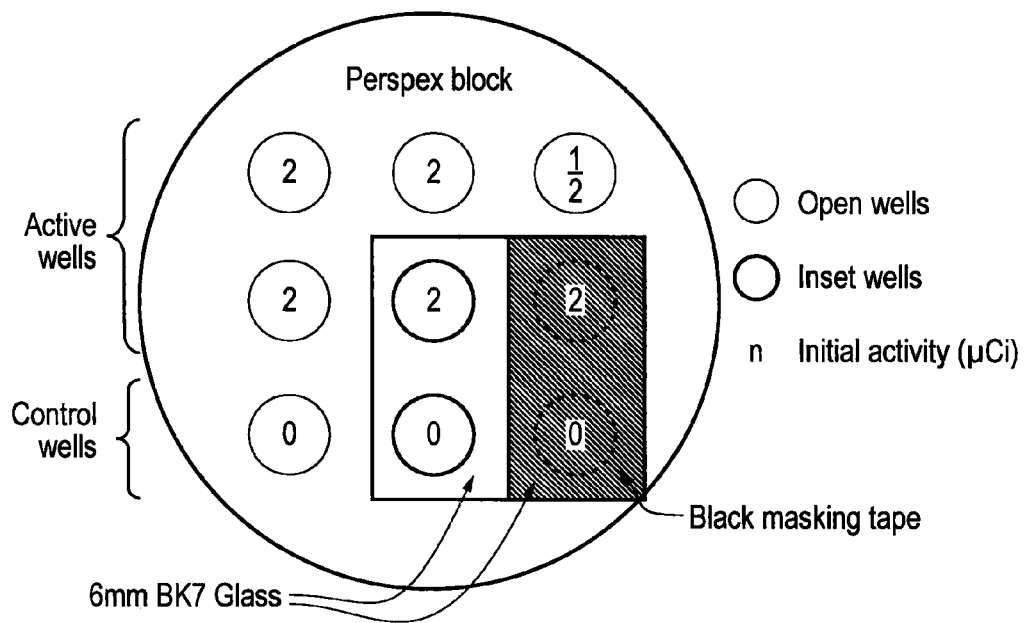
FIG. 7 shows the layout of sample wells used in the experiments.

The camera was set up so that the experiment could be conducted inside a lead enclosure with the operation of the laptop on the other side of a room. The camera had the following settings:

50 mm f/1.8 lens
CCD temperature: −80° C.
1 MHz pre-amplifier with a gain setting 3
0.5 µs vertical shift speed
300×EM Gain
The field of view is 47×47 mm
F18 was diluted and distributed into six 0.2 mL experimental wells inside a Perspex™ (PMMA) block. Three control wells with inactive material were also prepared. FIG. 7 illustrates the layout of the experimental wells.

The liquid volume and initial activity concentration in the active wells is shown in the table below.

| Activity (µCi) | Volume (µl) | Activity concentration (nCi/µl) | No. wells |
|---|---|---|---|
| 2 | 200 | 10 | 4 |
| 1 | 100 | 10 | 1 |
| 0.5 | 200 | 2.5 | 1 |

One control well and one active well with activity 2 µCi were covered with 6 mm thick BK7 glass. One control well and one active well with activity 2 µCi were covered with 6 mm thick BK7 glass and black masking tape. The BK7 glass is inset, with the wells under it 6 mm below the level of the other wells as viewed by the camera. The black masking tape was placed between the wells and the glass, leaving the glass open for viewing.

The sample block was prepared and placed under the shielded camera, which was then lowered into place and draped to give a light tight enclosure. Images with the following settings were acquired:

1. 1 s integration time, 16×16 resolution (32×32 binning)
2. 3 s integration time, 16×16 resolution (32×32 binning)
3. 5 s integration time, 32×32 resolution (16×16 binning)

Further images with the same settings were taken, with the room lights on and off, at regular intervals throughout the experiment.

After the experiment each image was exported and the raw data in counts is converted to a signal in photo-electrons (or detected photons) using the following formula:

$$\text{Signal(photoelectrons)} = \frac{(\text{Signal(counts)} - \text{Bias Offset}) \times \text{Conversion Factor}}{EM. \text{ Gain}}$$

Figure 8A:
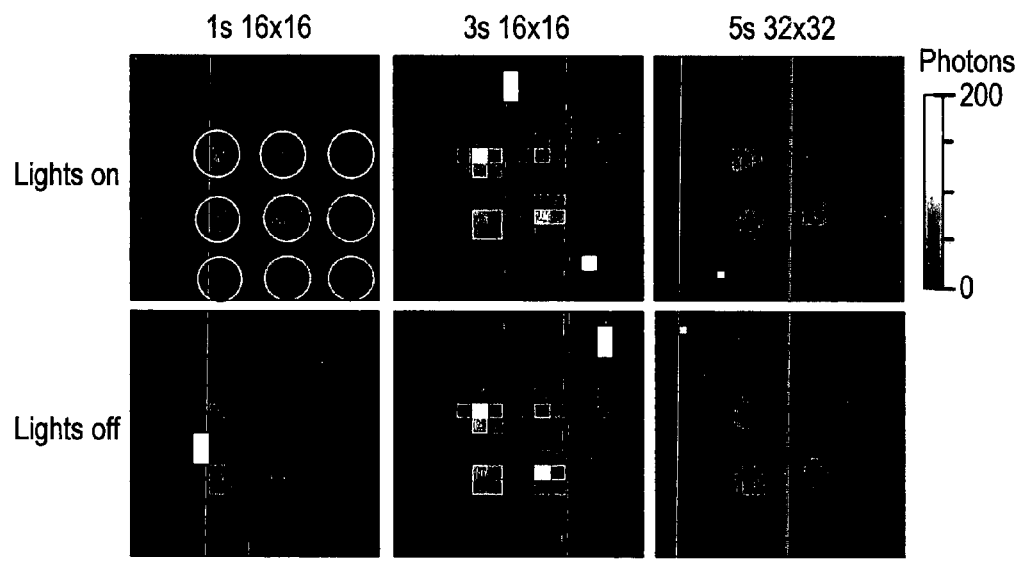
FIGS. 8a and 8b show Cerenkov images captured during the experiments.

Bias Offset=200 counts
Conversion Factor=4.27 electrons/count
EM Gain=300
Results FIG. 8a shows a set of images taken approximately 15 minutes into the experiment with the lights on and lights off. The positions of the wells have been circled in the top left image using the same scheme as FIG. 6. It can be seen that a higher resolution of 32×32 is obtainable in 5 seconds. In addition to the Cherenkov emission interference from high energy rays can be seen as random white pixels that have a signal level beyond the scale used.

Figure 8B:
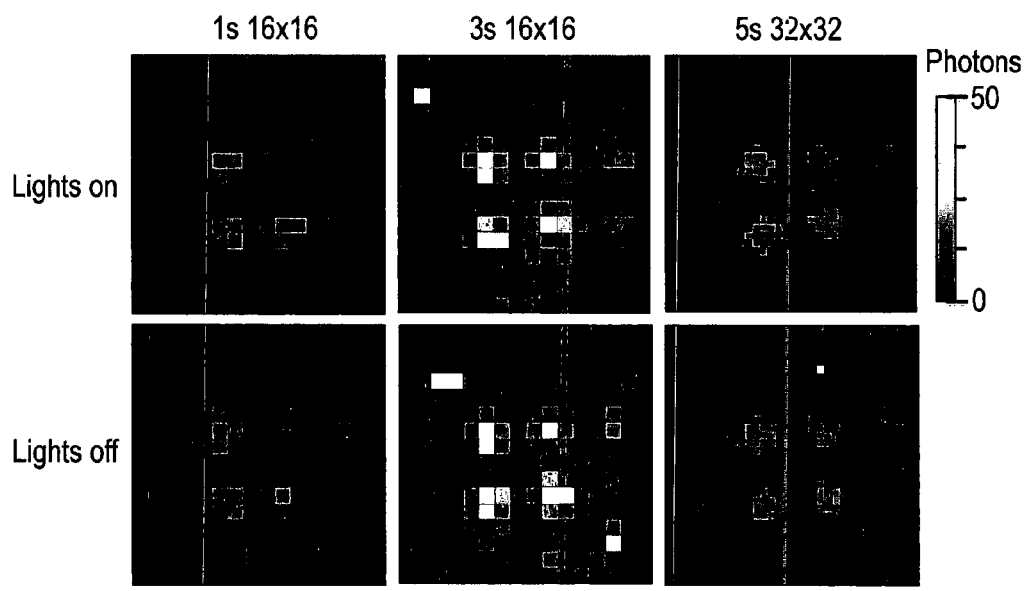

FIG. 8b shows set of images taken approximately 180 minutes into the experiment. Even with the lower signal levels there is no discernible difference due to the room lights. The higher activity wells are still easily visible and the lowest activity well is still discernible.

Figure 9:
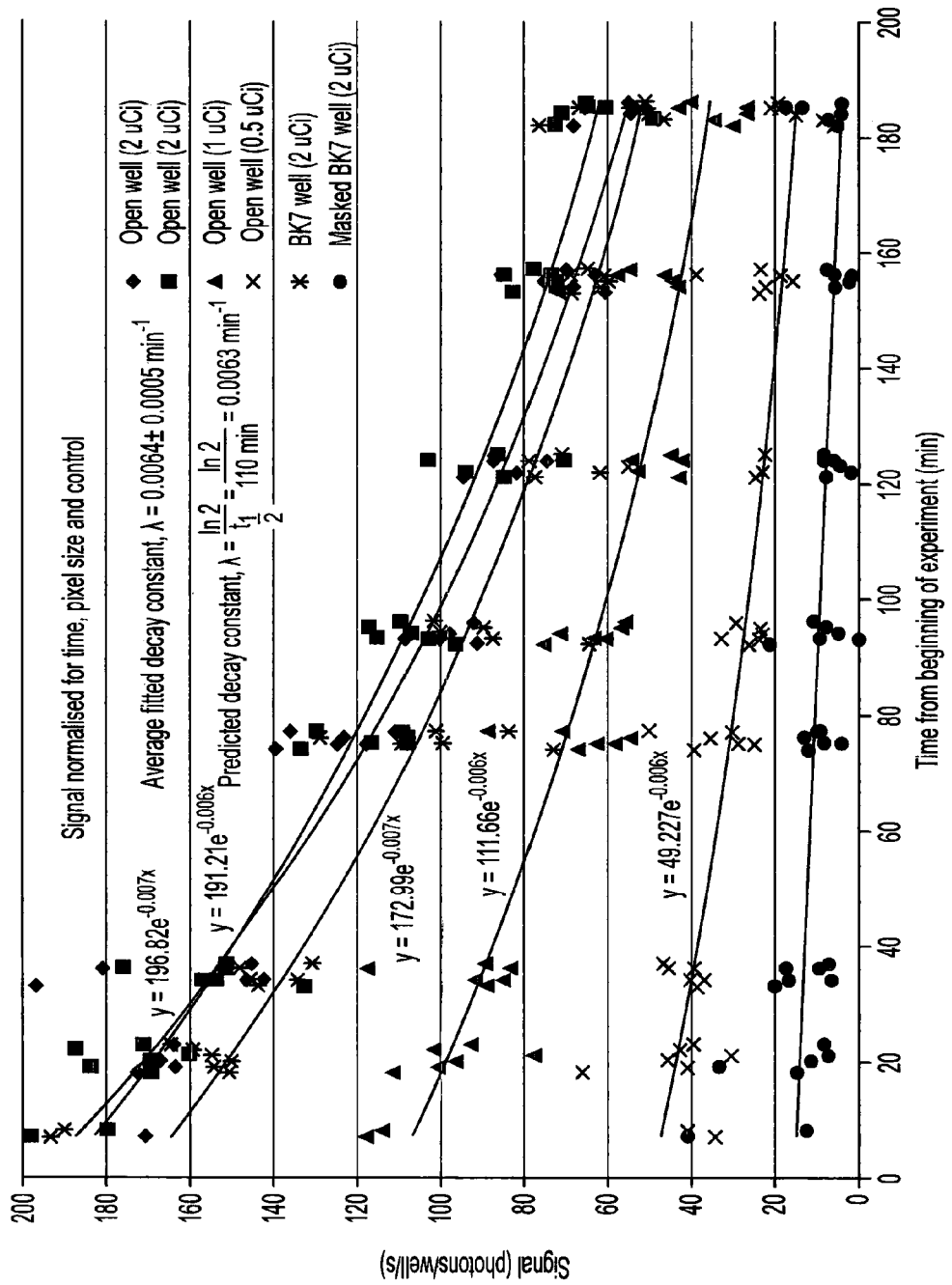
FIG. 9 is a graph of signal photon rate for each of the experimental wells.

FIG. 9 shows the signal photon rate for each active sample well, after correcting for the background by subtracting the corresponding control signal. Each point on the graph represents an image of the sample. The measured decay constant corresponds to a half-life of 108 minutes.

All three control samples showed no signal. The signal from the open wells was proportional to their initial activity. The signals showed exponential decay with a half-life matching that of the F18 FDG (110 minutes). Therefore, it was concluded that Cerenkov radiation due to activity of F18 FDG was being measured.

The active well covered by glass but not masked produced a similar signal to the open active wells. The masked well showed no visible signal, and was quantified to be 10% of the signal obtained from the unmasked well. Therefore it was concluded that the scintillation in optical BK7 glass was insignificant.

There was significant interference from gamma rays. However, it was shown in principle that higher resolutions are possible if the sensor is shielded from gamma rays and direct particle impingement. Further, it was possible to detect activities as low as 160 nCi (0.8 nCi/µl) with a spatial resolution down to 400 µm.

The invention claimed is:

1. Apparatus for optical imaging of Cerenkov luminescence from a sample subsequent to the sample receiving a dose of a radiopharmaceutical, the apparatus comprising:
   a light tight enclosure within which the sample can be received at a sample location;
   an imaging means outside of the enclosure, the imaging means for optical imaging of Cerenkov photons;
   a radiation shield disposed between the sample location in the enclosure and the imaging means, wherein the radiation shield is configured to protect the imaging means from radiation emitted from the sample; and
   one or more optical elements for guiding the light path of the Cerenkov photons emitted from the sample along a hollow optical conduit, the one or more optical components being arranged in the hollow optical conduit to turn the Cerenkov photons through an angle around the radiation shield, to the imaging means outside the enclosure.

2. Apparatus according to claim 1, wherein the imaging means is positioned and/or oriented relative to the sample location to minimise radiation impingement on the imaging means.

3. Apparatus according to claim 1, wherein the enclosure is a light tight specimen chamber.

4. Apparatus according to claim 3, where in the chamber comprises a door in a wall of the chamber that, when open, allows access to the inside of the chamber and when closed ensures a light tight seal with surrounding parts of the chamber to maintain the light tightness of the chamber interior for imaging the sample.

5. Apparatus according to claim 4, comprising a seal around the perimeter of the door to provide the light tight seal between the door and surrounding parts of the chamber wall when the door is closed.

6. Apparatus according to claim 5, wherein the position of the sample platform can be adjusted within the enclosure relative to the optical element.

7. Apparatus according to claim 3, comprising means within the chamber that can be used to confirm whether or not the chamber is light tight once the door is closed.

8. Apparatus according to claim 1, wherein the sample location is provided by a sample platform mounted within the enclosure on which the sample can be placed.

9. Apparatus according to claim 1, comprising a frame within which the sample is held at the sample location to prevent the sample from deforming and/or to spatially position and orient the sample.

10. Apparatus according to claim 1, wherein the imaging means is a CCD camera.

11. Apparatus according to claim 10, wherein the camera is an emCCD camera.

12. Apparatus according to claim 1, wherein the imaging means includes an image detector with a surface on which the Cerenkov photons impinge and the imaging means is oriented so that the image detector surface is substantially normal to a wall of the enclosure it is mounted adjacent to.

13. Apparatus according to claim 1, wherein the radiation shield surrounds a majority of the sides of the imaging means.

14. Apparatus according to claim 1, wherein the one or more optical elements for Cerenkov photons from within the light tight enclosure to the imaging means comprise a lens and a light tight optical conduit for Cerenkov photons collected by the lens to the imaging means.

15. Apparatus according to claim 14, wherein the focus of the lens can be varied and adjustment of the lens focus is motorised so that controls can be provided outside the enclosure to facilitate focusing the lens.

16. Apparatus according to claim 1, further comprising one or more lights within the enclosure that can illuminate the enclosure to facilitate acquisition of an illuminated image.

17. Apparatus according to claim 16, comprising a mechanical shutter to cover the light(s) during periods of CLI acquisition and to uncover the light(s) during periods of illuminated image acquisition.

18. Apparatus according to claim 17, wherein the mechanical shutter is arranged such that it is synchronised to an image acquisition sequence.

19. Apparatus according to claim 16, wherein the apparatus is controllably arranged such that duration on CLI acquisition periods is longer than illuminated image acquisition periods.

20. Apparatus according to claim 16, wherein the apparatus is controllably arranged such that there is a delay between illumination being removed from the enclosure and commencement of the CLI acquisition.

21. Apparatus according to claim 16, wherein the apparatus is controllably arranged such that a single imaging means is used to capture CLI images and illuminated images, the imaging means being switchable between an illuminated level image mode and a low light level image mode for capture of the illuminated and CLI images respectively.

22. Apparatus according to claim 21, wherein the apparatus is controllably arranged such that switching of the camera modes is synchronised with the switching on and off of the light(s) in the enclosure.

23. Apparatus according to claim 1, further comprising one or more ports in a wall of the enclosure that allow access for a hand or instrument without damaging the integrity of the light tight enclosure.

24. Apparatus according to claim 1, further comprising a Cerenkov radiator that can be placed over the sample in the enclosure.

25. The apparatus of claim 1, wherein the one or more optical components comprises a beam-splitter.

26. A method for optical imaging of Cerenkov luminescence from a sample subsequent to the sample receiving a dose of a radiopharmaceutical, the method comprising:
placing the sample in a light tight enclosure;
illuminating the interior of the enclosure with light and capturing an illuminated image of the sample in the enclosure whilst the interior of the enclosure is illuminated; and
capturing a Cerenkov luminescence image of the sample in the enclosure when the interior of the enclosure is not illuminated, wherein capturing the Cerenkov luminescence image comprises using one or more optical elements to guide the light path of the Cerenkov photons emitted from the sample along a hollow optical conduit, the one or more optical components being arranged in the hollow optical conduit to turn the Cerenkov photons through an angle around a radiation shield, to impinge on an imaging means outside the enclosure;
wherein the radiation shield is configured to protect the imaging means from radiation emitted from the sample.

27. A method according to claim 26, wherein a plurality of alternating illuminated and Cerenkov images are captured, the interior of the enclosure being intermittently illuminated, the illumination of the interior of the enclosure coinciding with capture of the illuminated images.

28. A method according to claim 26, wherein the illuminated image(s) and Cerenkov image(s) are overlaid.

29. A method according to claim 26, wherein the illuminated and Cerenkov images are captured by a single camera having two modes, one for capture of the illuminated image and one for capture of the Cerenkov image, the method comprising switching the camera between the two modes in synchronisation with the illumination of the interior of the enclosure.

30. A method according to claim 26 employing an apparatus in accordance with claim 1.

31. A method for optical imaging of Cerenkov luminescence from a sample subsequent to the sample receiving a dose of a radiopharmaceutical, the method comprising the steps of:
placing the sample in a light tight enclosure;
illuminating the sample with light from a light source located within the enclosure;
capturing a first image with a first imaging means whilst the sample is illuminated with white light from the light source, the first imaging means having a first dynamic range; and
capturing a second image with a second imaging means configured for Cerenkov luminescence imaging whilst the sample is not illuminated with light from the light source, the second imaging means having a second dynamic range;
wherein light paths feeding the first and second imaging means pass through optical elements such that the first and second imaging means both image the same region of the sample.

32. The method of claim 31 wherein the first image and the second image are superimposed.

33. The method of claim 31 wherein the sample is illuminated with light having a wavelength of between 500-740 nm.

34. The method of claim 31, wherein the sample is illuminated with light having a wavelength of between 435-500 nm.

35. The method of claim 31, including the step of applying strobed or spectrally separated lighting.

36. An apparatus for optical imaging of Cerenkov luminescence from a sample subsequent to the sample receiving a dose of a radiopharmaceutical, wherein the sample is intermittently illuminated with white light, the apparatus comprising:
a first imaging means for capturing a first image of the sample whilst the sample is illuminated, the first imaging means having a first dynamic range; and
a second imaging means configured for Cerenkov luminescence imaging for capturing a second image of the sample whilst the sample is not illuminated with said light, the second imaging means having a second dynamic range; and one or more optical elements, wherein light paths feeding the first and second imaging means pass through the optical elements such that the first and second imaging means both image the same region of the sample.

37. The apparatus of claim 36 wherein the apparatus comprises processing means to superimpose the two images.

38. The apparatus of claim 36, wherein the imaging means comprises a monochromatic camera capable of applying sequential red, green and blue illumination in any order, to provide a full-colour image.

39. The apparatus of claim 36, wherein the one or more optical components comprises a beam-splitter and wherein the light paths feeding the first and second imaging means coincide with the beam-splitter.

* * * * *